US00PP37401P2

(12) United States Plant Patent
Bergman

(10) Patent No.: US PP37,401 P2
(45) Date of Patent: Apr. 28, 2026

(54) SCAEVOLA PLANT NAMED 'SVAZ0009'

(50) Latin Name: *Scaevola aemula*
Varietal Denomination: SVAZ0009

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/342,846

(22) Filed: Sep. 29, 2025

(51) Int. Cl.
*A01H 6/00* (2018.01)
*A01H 5/02* (2018.01)

(52) U.S. Cl.
USPC ..... Plt./363

(58) Field of Classification Search
USPC ..... Plt./363
CPC ..... A01H 6/00; A01H 5/02
See application file for complete search history.

*Primary Examiner* — Keith O. Robinson
(74) *Attorney, Agent, or Firm* — Dale Skalla

(57) ABSTRACT

A new *Scaevola* plant named 'SVAZ0009' particularly distinguished by its pure white flowers with pale green-yellow eyes, continuous and an abundant flowering response, medium green foliage, a vigorous densely spreading growth habit with excellent branching and heat tolerance.

1 Drawing Sheet

Latin name of the genus and species of the plant claimed: *Scaevola aemula.*

Varietal denomination: 'SVAZ0009'.

BACKGROUND OF THE NEW PLANT

The present invention comprises a new *Scaevola*, botanically known as *Scaevola aemula*, and hereinafter referred to by the variety name 'SVAZ0009'.

'SVAZ0009' is a product of a planned breeding program. The new cultivar has pure white flowers with pale green-yellow eyes, continuous and an abundant flowering response, medium green foliage, a vigorous densely spreading growth habit with excellent branching and heat tolerance.

'SVAZ0009' originates from a hybridization in a field saran structure in August 2019 in Gilroy, California. The female parent was identified as 'White Touch', an unpatented commercially available variety having white flowers and a more open spreading plant habit. The male parent of 'SVAZ0009' is identified as '501-5' an unpatented, proprietary breeding line, having white flowers and a more compact growth habit.

The resulting seeds were sown in March 2020 and 'SVAZ0009' was selected as one flowering plant within the progeny of the stated cross in August 2020 in a greenhouse in Gilroy, California.

The first act of asexual reproduction of 'SVAZ0009' was accomplished when vegetative stem cuttings were propagated from the initial selection in November 2020 in a controlled environment in Gilroy, California.

BRIEF SUMMARY OF INVENTION

Horticultural examination of plants grown from cuttings of the plant initiated in November 2020 in Gilroy, California, and continuing thereafter, has demonstrated that the combination of characteristics as herein disclosed for 'SVAZ0009' are firmly fixed and are retained through successive generations of asexual reproduction.

'SVAZ0009' has not been observed under all possible environmental conditions. The phenotype may vary significantly with variations in environment such as temperature, light intensity and day length.

A Plant Breeder's Right for this cultivar has not yet been applied for. 'SVAZ0009' has not been made publicly available prior to the effective filing date of this application, notwithstanding any disclosure that may have been made less than one year prior to the effective filing date of this application by the inventor or another who obtained 'SVAZ0009' directly from the inventor.

The following traits have been repeatedly observed and are determined to be basic characteristics of the new variety. The combination of these characteristics distinguishes this *Scaevola* as a new and distinct variety.

BRIEF DESCRIPTION OF THE PHOTOGRAPHS

The accompanying photographic drawings show typical flower and foliage characteristics of 'SVAZ0009' with colors being as true as possible with an illustration of this type.

Figure 1:
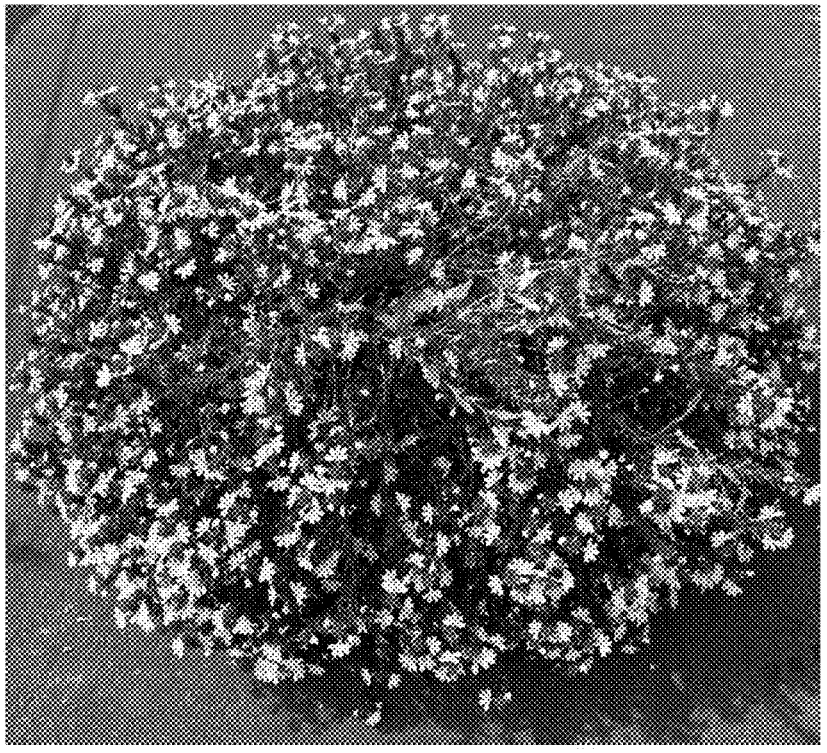
Figure 2:
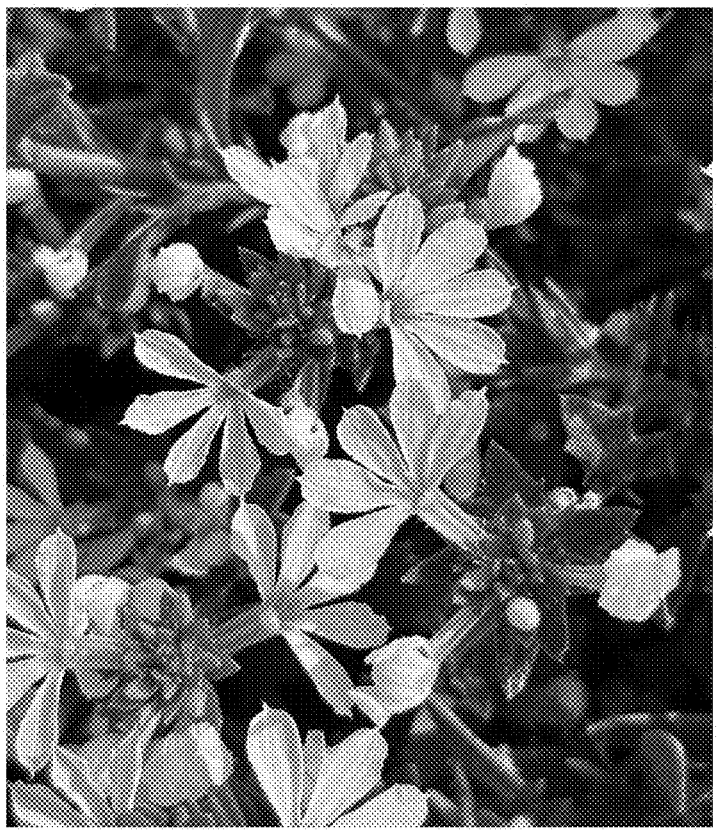

The photographic drawings show in FIG. 1, a six month old a flowering plant of the new variety growing in an outdoor field and in FIG. 2, a close-up of the flowers.

DETAILED BOTANICAL DESCRIPTION

The aforementioned photographs were taken September 2025 in Gilroy, California. The following botanical description was prepared using the same plants as depicted in the photographs. The plants were growing in an outdoor field. They were about 6 months in age.

Color references are made to The Royal Horticultural Society Colour Chart (R.H.S.) 2015.

TABLE 1

DIFFERENCES BETWEEN THE NEW VARIETY 'SVAZ0009' AND A SIMILAR VARIETY

| | 'SVAZ0009' | 'Surdiva ® White Improved', Unpatented |
|---|---|---|
| Flower petal apex: | Apiculate | Aristate |
| Foliage width: | Broader | More narrow |
| Stem diameter: | Larger about 0.3 cm | Smaller about 0.25 |
| Flower horizontal diameter: | Smaller | Larger |

Plant:

*Form, growth and habit.*—Herbaceous perennial. Dense and spreading, growing wider than tall. For outdoor use in ground, containers, or hanging baskets. Time for producing a commercial, flowering plant approximately is 12 weeks for one plant in a quart size container.

*Plant height.*—23 cm.

*Plant height (inflorescence included).*—23 cm.

*Plant width.*—86 cm.

Roots:

*Number of days to initiate roots.*—About 10 days at about 21 degrees C.

*Number of days to produce a rooted cutting plant.*—3.5 weeks at about 22 degrees C.

*Type.*—Fibrous, and self-branching.

*Color.*—RHS 155D.

Foliage:

*Arrangement of leaves.*—Alternate.

*Immature leaf, color upper surface.*—RHS 137B.

*Immature leaf, color lower surface.*—RHS 137C.

*Mature leaf, color upper surface.*—RHS 137A.

*Mature leaf, color lower surface.*—RHS 137C.

*Length.*—2.0-8.3 cm.

*Width.*—0.7-3.8 cm.

*Shape.*—Spatulate.

*Base shape.*—Acute.

*Apex shape.*—Acute.

*Margin.*—Irregularly dentate.

*Texture, upper surface.*—Leathery, pubescent.

*Texture, lower surface.*—Leathery, pubescent.

*Pattern of leaf veins.*—Pinnate.

*Color of veins, upper surface.*—RHS 137A.

*Color of vein (midrib), lower surface.*—RHS 137C.

*Petiole attachment.*—Sessile.

Stem:

*Branching characteristics.*—Very free branching with lateral branches forming at potentially every node.

*Quantity of main branches per plant.*—10-13.

*Color of stem.*—RHS 138A.

*Length of stem.*—24-42 cm.

*Diameter (at about mid point).*—0.3 cm.

*Length of internodes.*—1.2-5.9 cm.

*Stem, texture.*—Glabrous.

Inflorescence:

*Type of inflorescence.*—Solitary sessile flowers, emerging from leaf axils with one flower per leaf axil stem. Indeterminate.

*Number of flower per inflorescence.*—1, with 3-5 flowers open per stem.

*Blooming habit.*—Continuously from spring through fall.

*Quantity of flowers per plant.*—About 450 in various stages of development.

*Lastingness of individual blooms on the plant.*—Approximately 6-8 days, depending on temperature.

*Fragrance.*—Absent.

*Peduncle.*—None. Flowers are sessile.

Bud (just before opening/showing color):

*Color.*—RHS 145B.

*Length.*—1.4 cm.

*Width.*—0.25 cm.

*Shape.*—Lenticular.

Immature flower:

*Diameter.*—2.0 cm.

*Vertical diameter.*—2.0 cm.

*Color upper surface.*—RHS 155D.

*Color lower surface.*—RHS 155D.

Mature flower:

*Shape.*—Composed of 5 petals fused at the base and in a semicircular or fan-like arrangement to form a lower part which is open tube-shaped; the petals are situated at obtuse angles to the flower base and minimally overlap.

*Flower, horizontal diameter.*—2.1 cm.

*Flower, vertical diameter.*—2.2 cm.

*Flower, diameter of the funnel.*—0.3 cm, open tube.

*Flower color, upper surface.*—RHS 155D.

*Flower color, lower surface.*—RHS 155D.

*Color of the funnel, inner side.*—RHS 145C.

*Color of the funnel, outside.*—RHS 145C.

*Petal shape.*—Roughly elliptical with pointed tips.

*Petal apex shape.*—Apiculate.

*Petal base shape.*—Fused.

*Petal margin.*—Entire.

*Petal length, from the corolla opening.*—0.9 cm.

*Petal width, maximum.*—0.45 cm.

*Throat diameter.*—0.5 cm.

*Throat texture.*—Pubescent.

*Corolla, texture of upper surface.*—Glabrous, smooth.

*Corolla, texture of lower surface.*—Glabrous, smooth.

*Tube length.*—1.2 cm.

*Tube texture.*—Pubescent.

*Pedicel, color.*—Not present. Sessile.

Calyx:

*Form.*—Composed of one larger and somewhat fleshy sepal and two narrow sepals at the base of the flower.

*Color, visible outer surface.*—RHS 138A.

*Length.*—1.1-1.7 cm.

*Width.*—0.3-0.6 cm.

*Shape.*—Lanceolate for the larger sepal and ligulate for the narrow sepals.

*Apex shape.*—Narrowly acute.

*Base.*—Sessile.

*Margins.*—Entire.

*Texture, upper surface.*—Puberulent.

Reproductive organs:

Gynoecium:

*Pistil.*—1.

*Style length.*—0.8 cm.

*Diameter.*—0.05 cm.

*Style color.*—RHS 149C.

*Stigma color.*—RHS 149D, not visible. Located inside the indusium.

*Indusium color.*—RHS 158A.

*Stigma shape.*—Linear.

*Ovary color.*—RHS 149C.

Androecium:

*Stamens*.—5, protruding from the flower throat.

*Filaments*.—Fused with the base of the flower.

*Anther*.—Narrow, ovate.

*Anther color*.—RHS 4D.

*Anther length*.—0.15 cm.

*Color of pollen*.—RHS 4D.

*Pollen amount*.—Sparse.

Fertility/seed set: Moderate.

Disease/pest resistance: Has not been observed on this hybrid.

What is claimed is:

1. A new and distinct variety of *Scaevola* plant named 'SVAZ0009', substantially as illustrated and described herein.

* * * * *